United States Patent [19]
Paul et al.

[11] Patent Number: 6,156,541
[45] Date of Patent: Dec. 5, 2000

[54] COMPOSITIONS AND METHODS FOR CATALYZING HYDROLYSIS OF HIV GP120

[75] Inventors: Sudhir Paul; Ravishankar Kalaga, both of Omaha, Nebr.

[73] Assignee: The Board of Regents of the University of Nebraska, Omaha, Nebr.

[21] Appl. No.: 09/000,023

[22] PCT Filed: Jul. 19, 1996

[86] PCT No.: PCT/US96/12025

§ 371 Date: Jan. 21, 1998

§ 102(e) Date: Jan. 21, 1998

[87] PCT Pub. No.: WO97/03696

PCT Pub. Date: Feb. 6, 1997

Related U.S. Application Data

[60] Provisional application No. 60/001,321, Jul. 21, 1995.

[51] Int. Cl.$^7$ ............................ C12P 21/00; C12P 21/08; C07K 16/10
[52] U.S. Cl. ..................... 435/69.6; 435/188.5; 530/412; 530/413
[58] Field of Search ........................ 424/148.1; 435/69.6, 435/188.5; 530/412, 413

[56] References Cited

FOREIGN PATENT DOCUMENTS

WO8910754  11/1989  WIPO .
WO9317124   9/1993  WIPO .

OTHER PUBLICATIONS

Fahey et al., *Clin Exp. Immunol.* 88:1–5, 1992.
Fox, J.L., *Bio/Technology* 12:128, Feb. 1994.
Haynes et al., *Ann. Med.* 28:39–41, 1996.
Moreira et al., *IXth Int.'l. Conf. AIDS*, Berlin, Jun. 6, 1993, Abstract No. PO–A29–0700.

Qing–Sheng Gao, et al. Molecular Cloning of a Proteolytic Antibody Light Chain. *The Journal of Biological Chemistry.* 1994 269: 32389–32393.

K. Muraszko, et al. Pharmacokinetics and Toxicology of Immunotoxins Administered into the Subarachnoid Space in Nonhuman Primates and Rodents. *Cancer Research.* Aug. 15, 1993 53:16; 3752:7.

Bonnie L. Bermas, et al. Binding of Glycoprotein 120 and Peptides from the HIV–1 Envelope by Autoantibodies in Mice with Experimentally Induced Systemic Lupus Erythematosus and in Patients with the Disease. *Aids Research and Human Retroviruses.* 1994. 10:9.

Sherie L. Morrison, et al. Genetically Engineered Antibodies and Their Application to Brain Delivery. *Advanced Drug Delivery Reviews.* 1995. 15:147–175.

Sudhir Paul, et al. Characterization of Thyroglobulin–Directed and Polyreactive Catalytic Antibodies in Autoimmune Disease. *The Journal of Immunology.* 1997. 159:1530–1536.

Sonia Tyutyulkova, et al. Efficient Vasoactive Intestinal Polypeptide Hydrolyzing Autoantibody Light Chains Selected by Phage Display. *Elsevier Science.* 1996. BBA-DIS 61583.

Sudhir Paul, et al. Natural Catalytic Antibodies: Pepetide–hydrolyzing Activities of Bence Jones Proteins and $V_L$ Fragment. *The Journal of Biological Chemistry.* 1995. 270:15257–15261.

*Primary Examiner*—Robert D. Budens
*Attorney, Agent, or Firm*—Dann, Dorfman, Herrell and Skillman

[57] ABSTRACT

A catalytic antibody and components thereof which cleave HIV gp120 are disclosed. Methods of isolating, cloning and purifying such antibodies or antibody components from patients are also described. The compositions described may provide utility in the treatment of HIV infection.

17 Claims, 10 Drawing Sheets

COMPOSITIONS AND METHODS FOR CATALYZING HYDROLYSIS OF HIV GP120

This application is the U.S. National Phase of International Application PCT/US96/12025, filed Jul. 19, 1996, which claims priority under 35 U.S.C. § 119(e) to U.S. Provisional Application 60/001,321, filed Jul. 21, 1995.

FIELD OF THE INVENTION

This invention relates to treatment of HIV infection and associated pathologies. In particular, catalytic (proteolytic) antibodies, or derivative thereof, are provided, which catalyze the hydrolysis of the HIV gp120 protein.

BACKGROUND OF THE INVENTION

The envelope glycoproteins of HIV-1 are initially synthesized as a single 160 kD precursor, gp160, which is cleaved at the Arg511-Ala512 bond by a cellular protease, producing gp120 and the integral membrane protein gp41 (Kido, H., et al., J. Biol. Chem. 268:13406–13413 (1993)). The biological activity of gp120 is a key ingredient in initial binding of host cells by HIV-1, propagation of the virus and its toxic effects on uninfected neurons and other cells (Kieber-Emmons, T., et al., Biochim. Biophys. Acta. 989:281–300, (1987); Capon et al., Ann. Rev. Immunol. 9:649–678). Thus, gp120 is a target of passive and active immunization against AIDS (Kahn, J. O., et al., J. Infec. Dis. 170:1288–1291 (1994); Birx, D. L., et al., Curr. Opin. Immunol. 5:600–607 (1993); Berman, P. W., et al., Proc. Natl. Acad. Sci. USA 85:5200–5204 (1988)). Binding of a conformational epitope of gp120 to CD4 receptors on host cells is the first step in HIV-1 infection. Individual amino acids constituting this epitope appear to be located in the second (C2), third (C3), and fourth (C4) conserved gp120 segments (Olshevsky, T. J., et al., J. Virol. 64:5701–5705 (1990)). These are gp120 residues 256, 257, 368–370, 421–427 and 457. Monoclonal antibodies that bind the CD4 binding site have been described (Thali, M., et al., J. Virol. 65:6188–6193 (1991); Thali, M., et al., J. Virol. 66:5635–5641 (1992)). Since the CD4 binding site is a conformational epitope, distant residues that are not themselves constituents of the epitope may be important in maintaining the ability to bind CD4. Gp120 interactions with other host cell proteins are also essential for virus propagation. For example, binding of gp120 by calmodulin may be involved in HIV-1 infectivity, as revealed by the inhibitory effect of calmodulin antagonists (Srinivas, R. V., et al., AIDS Res. Hum. Retroviruses 108:1489–1496 (1994). Asp180 located between the V1 and V2 regions of gp120 is critical for viral replication (Wang, W-K., et al., J. Virol. 69:538–542 (1995)). Similarly, the V3 loop is essential for infectivity (Ivanoff, L. A., et al., Virology 187:423–432 (1992)). It is clear, therefore, that structural determinants in gp120 other than those constituting the CD4 binding site are likely to be necessary for virus genome replication, coat protein synthesis and virus particle packaging.

Shedding of gp120 by virus particles and infected cells has been proposed as a factor in the pathogenesis of AIDS (Gelderblom, H. R. et al., Lancett ii:1016–1017 (1985)). Purified gp120 is toxic for cultured neurons (Brenneman, D. E. et al., Nature 335:639–642 (1988); Muller, W. E. G. et al., Eur. J. Pharmacol 226:209–214 (1992)). Uninfected T-lymphocytes coated with gp120 can be lysed by antibody-dependent monocytes (Hober, D. et al., FEMS Immunol. Med. Microbiol. 10:83–92 (1995)). Uninfected CD4+ cells can die because binding of the gp120-gp41 complex induces apoptosis (Laurent-Crawford, A. G. et al., Res. Virol 146:5–17 995)). Gp120 also binds complement components (Stoiber, H. et al., AIDS 9:19–26 (1995)).

There has been considerable interest in the possibility that gp120 contributes to neural damage observed in AIDS patients (Everall, I. P et al., J. Neuropathol. Exp. Neurol. 52:561–566 (1993)). Productive infection in the brain occurs in a relatively small number of cells, which include microglia, multinucleated giant cells and blood-derived macrophages (Epstein. L. G et al., Ann. Neurol. 33:429–436 (1993)). Yet, there is wide-spread brain damage at areas that are not infected by the virus. This has lead to suggestions that soluble gp120 shed by the virus and cytokines produced by infected cells may be responsible for the damage (Lipton, S. A., Brain Pathol. 1:193–199 (1991), Giulian, D. et al., Science 250:1593–1595 (1990); Benos, D. J. et al., Proc. Natl. Acad. Sci. USA 91:494–498 (1994)). The neurotoxic effects of gp120 may be indirect, involving stimulation of the NMDA receptor (Benos, D. J. et al., Proc. Natl. Acad. USA 91:494–498 (1994)) or induction of cytokines (Yeung, M. C. et al., AIDS 9:137–143, (1995)). Gp120 also stimulates neurotoxin release from monocytes (Giulian, D. et al., Proc. Natl Acad. Sci. USA 90:2769–2773, (1993)), indicating that its neurotoxic effects may require the participation of this cell type. The evidence for neurotoxicity of soluble gp120 includes:

(a) transgenic mice expressing gp120 in the brain show widespread neuronal damage (Toggas, S.M. et al., Nature 367:188–193 (1994));

(b) pure gp120 at sub-picomolar concentrations kills cultured astrocytes and cerebral cortical cells ((Brenneman, D. E. et al., Nature 335:639–642 (1988); Muller, W. E. G. et al., Eur. J. Pharmacol 226:209–214 (1992)).);

(c) injections of pure gp120 in vivo produce brain damage (Hill, J. M. et al., Brain Res. 603:222–223 (1993));

(d) a gp120-like neurotoxic activity present in spinal fluid has been described (Buzy, J. et al., Brain Res. 598:10–18 (1992));

(e) peptide-T, an octapeptide corresponding to a segment of gp120 and bearing some homology to the neuropeptide VIP, may ameliorate neuronal dysfunction in AIDS patients (Bridge, T. P. et al., Psychopharmacol. Bull 27:237–245 (1991)).

gp120 expresses many linear and conformational antigenic epitopes to which antibodies are made. These include neutralizing antibodies made by HIV-infected individuals to the V3 loop (Dreyer, E. B. et al., Science 248:364–367 (1990); Meylan, P. R. et al., AIDS 6:128–130 (1992); Pollard, S. et al., Proc. Natl. Acad. Sci. USA 88:11320–11324 (1991)). Because the V3 loop is a hyper-variable region, these antibodies are type-specific, with neutralizing activity directed only against HIV variants with V3 sequences similar to the virus strain responsible for initial infection. On the other hand, antibodies made in the later stages of the disease can be broadly protective, as measured by inhibition of the ability of different HIV-1 strains to infect susceptible cell lines and primary lymphoid cell cultures in vitro. A subset of these protective antibodies are directed against conserved regions of gp120 essential for binding the CD4 receptor and virus propagation (Hattori, T. et al., FEBS Lett 248:48–52 (1989); Schulz, T. et al., AIDS Res. Hum. Retroviruses 9:159–166 (1993); Clements, G. J. et al., AIDS Res. Hum. Retroviruses 7:3–16 (1991)). It is widely believed that recruitment of neutralizing antibody responses to the conserved regions of gp120 will be necessary for effective vaccination against AIDS. Similarly, the success of passive immunization with antibodies will depend on the ability to recognize conserved gp120 regions.

Others have observed that autoantibodies found in systemic lupus erythematosus patients are able to bind gp120 (Gu, R. et al., AIDS Res. Hum. Retroviruses 9:1007–1015 (1993; Callebaut, C, et al., Science 262:2045–2050 (1993)). Cross-reactivity between antibodies to gp120 and to HLA class I heavy chains (H-chains) has been suggested (Sattentau, Q. J. et al., J. Virol. 67:7383–7393 (1993)). AIDS patients have also been described to express DNA-hydrolyzing catalytic antibodies (Woolley, D. W. et al., John Wiley & Sons, Inc. 1952 pp 82).

Speculations that antibodies may develop catalytic activity date back to Woolley in 1952 (Gao, Q. S., et al., J. Biol. Chem 269:32389–32393 (1994)) who suggested that if exposed to an antigen for a sufficiently long period, the immune system may synthesize catalytic antibodies. A detectable sequence homology exists between antibody L-chains and serine proteases (Sun, M. et al., J. Biol. Chem 269:734–738 (1994)). Kohen et al. reported that immunization with steroids or dinitrophenol conjugated to carrier proteins provoked the formation of antibodies with esterase capabilities (Sun, M. et al., J. Immunol 153:5121–5126 (1994); Paul, S. et al., Appl. Biochem. Biotechnol. 47:241–255 (1994)). Human autoantibodies that hydrolyze the neuropeptide VIP have been demonstrated (Li, L., et al., Mol. Immunol. 1996, In press.). Autoantibody catalyzed hydrolysis of VIP has been reproduced (Li, L. et al., J. Immunol. 154:3328–3332 (1995)). Other groups have shown autoantibody mediated hydrolysis of DNA (Tyutyulkova, S. et al., Biochimica Biophysica Acta 1996, In press.; Kalaga, R. et al., J. Immunol 155:2695–2702 (1995)).

Antibodies with enzymatic activity offer the possibility of specific, high efficiency catalytic chemical conversion of ligands. Many biological mediators are peptides or proteins, including the antigens of pathogenic organisms, hormones, neurotransmitters and tumor specific antigens. It is possible to utilize the vast repertoire of specificities that the immune system encompasses to catalyze chemical reactions not within the scope of naturally occurring enzymes. The combination of antibody specificity with the catalytic power of enzymes has the potential of generating potent therapeutic agents, i.e., catalytic antibodies capable of specifically hydrolyzing key viral envelope proteins.

SUMMARY OF THE INVENTION

A cure for HIV infection has not yet been developed. Treatments available to date are directed to inhibition of viral replication to prolong the latency period of the illness. The present invention provides methods and compositions that may be used in AIDS patients to reduce the level of HIV and soluble gp120 in the body. Administration of these compositions to patients may alleviate the neurological symptoms of patients suffering from AIDS related dementia.

The present invention comprises hydrolytic anti-gp120 antibodies and L chain antibody components isolated from patient sera that efficiently cleave gp120 into inactive subfragments. Methods are provided for the isolation of and purification of catalytic antibodies and antibody components that mediate hydrolysis of gp120.

Preferred embodiments of the invention are antibodies and antibody components produced using recombinant methods. Following screening of sera for gp120 cleavage activity, peripheral blood lymphocytes are isolated and used as a source of mRNA encoding the activity for cDNA library generation. Isolation of genes encoding the catalytic antibodies and antibody components of the invention is performed using methods well known to those skilled in the art. Phage display of the L chains of the invention for isolation of L chain expressing clones is contemplated. Also envisioned is cloning of the immune repertoire from lymphocytes isolated from HIV-1 and SLE patients using primers to conserved regions of IgG genes.

Following isolation, expression and purification of recombinant gp120 hydrolyzing antibodies or antibody components, methodology for administration to HIV-infected patients is provided. The catalytic gp120 cleaving antibody or components thereof may administered i.v. in a suitable pharmaceutical preparation. Alternatively, the gp120 hydrolytic antibodies of the invention may be administered to the intraventricular compartment of the brain via a cannula. The catalytic L chains of the invention may also be translationally fused to transferrin to mediate passage of the blood brain barrier in patients infected with HIV-1.

DETAILED DESCRIPTION OF THE INVENTION

The unanticipated discovery that a normal human protein is capable of specifically recognizing gp120 and catalyzing lysis of a peptide bond in gp120 opens the possibility of developing a new therapeutic intervention in acquired immunodeficiency syndrome (AIDS). An anti-gp120 hydrolytic antibody may be used pharmacologically in the treatment of AIDS patients, for example in the treatment of AIDS-related dementia. Preliminary data have indicated that anti-gp120 proteolysis eliminates gp120-mediated neurotoxicity. Another and more direct application would be as an injectable protein solution that by binding to and cleaving gp120 would diminish HIV infectivity, either by destroying the gp120 receptor binding site, or by destabilizing the viral receptor binding site. The hydrolytic gp120 antibody may be used as an immune system supplement to enhance the ability of the body's natural mechanisms to control the disease. One of the L-chains with gp120 hydrolyzing activity exemplified in this application was isolated from a multiple myeloma patient (Lay2). The original antigenic stimulus responsible for the specificity of the myeloma L-chain is unknown. The reaction of the L-chain with gp120 may reflect a cross-reactivity phenomenon, due to chance structural fit between the binding site and gp120. At the time of the death of this patient, AIDS was not a recognized clinical entity and it is not known whether the patient was positive for HIV-1 antibodies. Multiple myeloma can occur at increased frequency in AIDS patients (Erhan, S., et al., Nature 251:353–355 (1974), but there is no evidence that the donor of the catalytic L-chain had AIDS.

Recent reports have demonstrated that HIV infection involves a balance between rapid HIV replication and high turnover of CD4 T-cells (Wei et al., Nature 373: 117–122, 1995; Ho et al., Nature 373: 123–126, 1995). Aggressive viral-specific proteolytic treatment at this stage, when the immune system is still strong and containing the infection, would enhance the possibility of elimination of the infection, or extend the period of latency.

The following examples are provided to describe the invention in greater detail. They are not intended to limit the invention in any way.

EXAMPLE I

ANTIBODY L CHAIN MEDIATED HYDROLYSIS OF GP120

Figure 1:
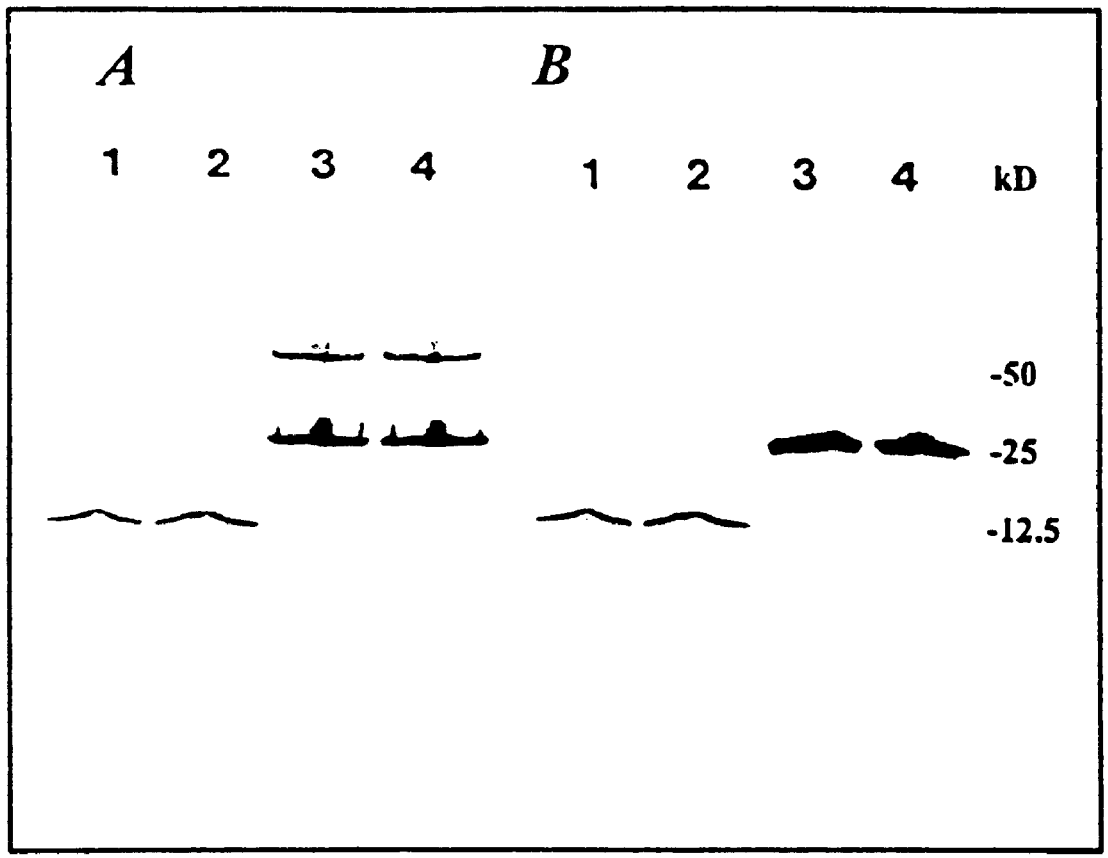
FIG. 1 is a silver stained gel of Bence Jones proteins and their $V_L$ domains run under reducing (A) and non-reducing (B) conditions.

Twenty nine monoclonal antibody L chains purified from patients with multiple myeloma have been described (Solomon, A., Meth. Enzym. 116:101–121 (1985); samples provided by Dr. Solomon, University of Tennessee), a recombinant L-chain with VIP hydrolyzing activity (Gao, Q-S., et al., J. Biol. Chem. 269:32389–32393 (1994)) and polyclonal anti-VIP antibodies (Paul, S., et al., J. Biol. Chem. 266:16128–16134 (1991) were screened for the ability to hydrolyze $^{125}$I-labeled gp120. Radiolabeling of electrophoretically pure gp120 (IIIB; AIDS Research and Reference Reagent Program, NIH) was by the chloramine-T method, followed by purification of $^{125}$I-gp120 by gel filtration. A single band of radiolabeled gp120 at 120 kD was observed by SDS-PAGE and autoradiography. FIG. 1 is a silver-stained SDS-PAGE gel showing the purity of the L chain preparation. The L chains were incubated with $^{125}$I-gp120 and the reaction mixtures were analyzed by SDS-polyacrylamide gel electrophoresis and quantitative autoradiography (Brugger, C., et al., J. Biol. Chem. 266:18358–18362 (1991). One human monoclonal L-chain with gp120 hydrolyzing activity was identified (Lay2). The remaining L chains and anti-VIP antibodies were devoid of activity. The gp120 hydrolyzing activity coeluted from a gel filtration column with the L-chain protein peak. Nearly equivalent cleavage of gp120 by Lay2 was observed in physiological buffers and nutrient media (phosphate buffered saline (PBS), Hank's buffered saline solution (HBSS) and RPMI 1640). Four radiolabeled gp120 cleavage products of mass approximately 80 kD, a smear around 50 kD, 20 kD, and <6 kD were evident by nonreducing electrophoresis. See FIG. 2A. The 80 kD band appeared to undergo fragmentation under reducing conditions, suggesting that it contained disulfide bonded fragments. Identical product profiles were observed using $^{125}$I-gp120 preparations derived from HIV-1 strains IIIB, SF2 and MN. The radiolabeled 80 kD band appeared to undergo further digestion upon prolonged incubation for up to 36 hours. The cleavage profiles of unlabeled gp120 and radiolabeled gp120 were similar, except that the intensities of the individual bands were different, which is probably a reflection of the methods used for detection of the two types of substrates (silver-staining versus $^{125}$I-labeling at Tyr residues followed by autoradiography). Unlabeled gp120 isolated from HIV-1 strains IIIB, SF2 and MN was hydrolyzed to similar levels (50, 44 and 60%, respectively) by Lay2 (250 nM; 6 hours), and estimated by quantitative scanning of the band intensities.

Figure 2B:
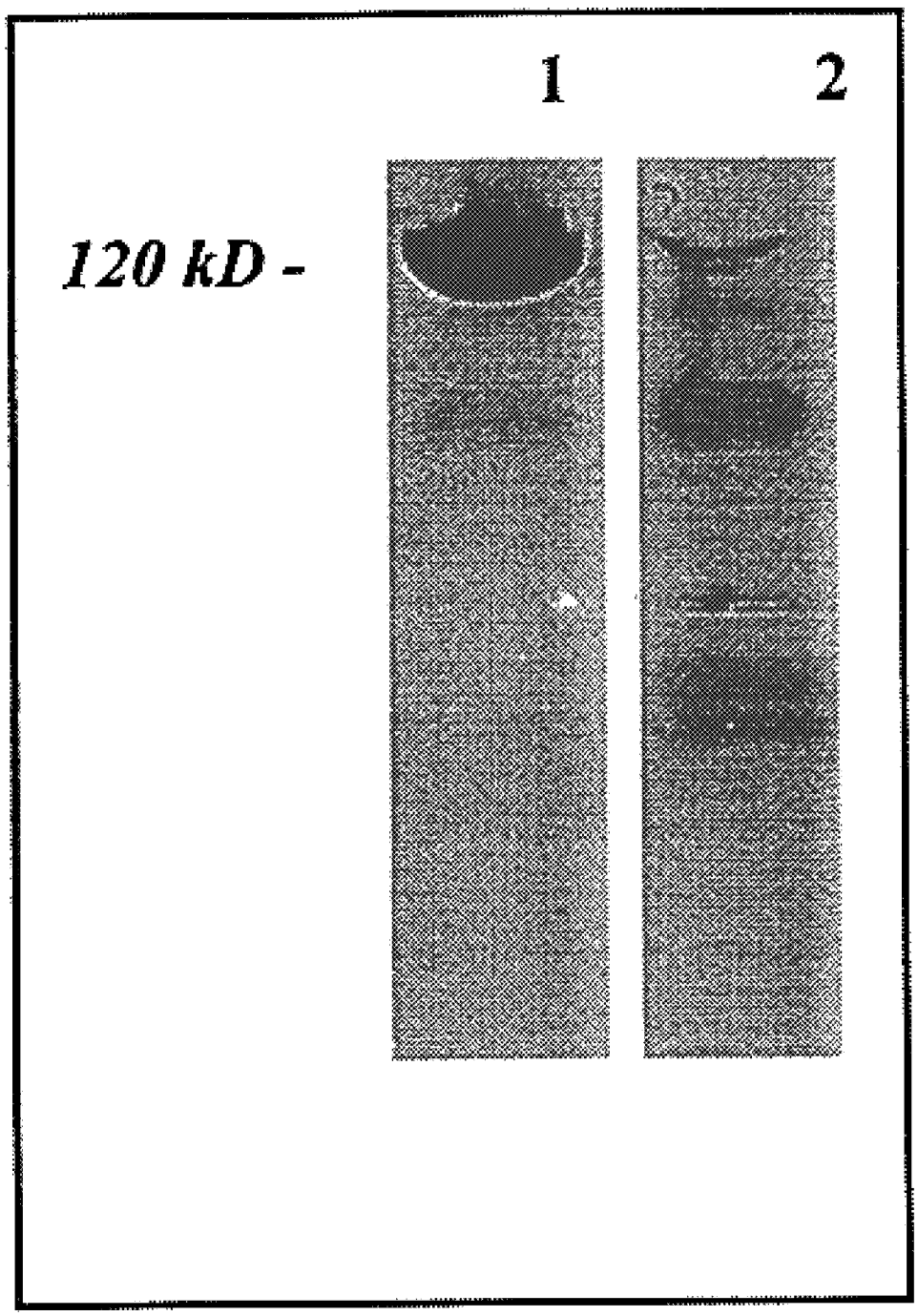
Figure 3:
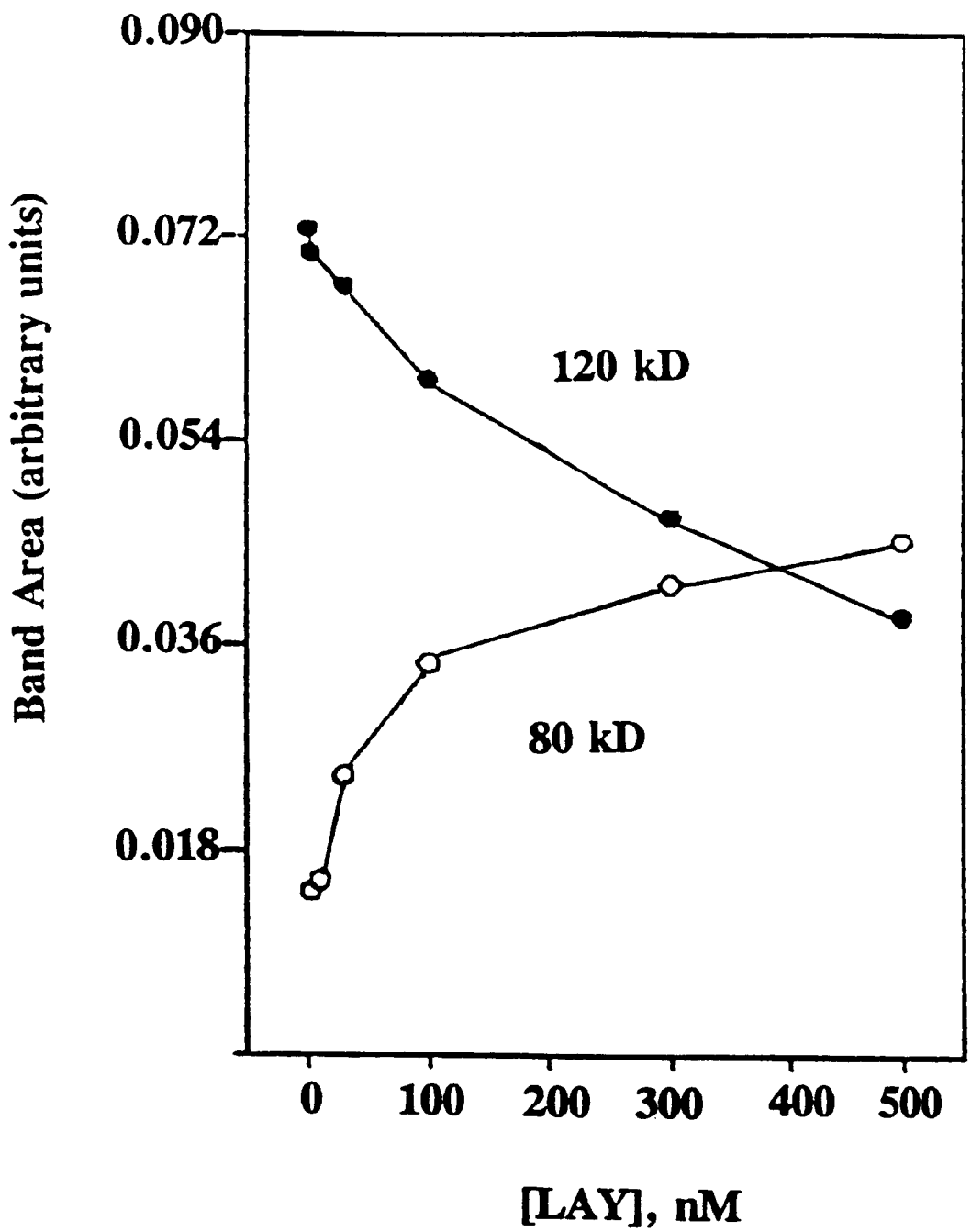
FIG. 3 is a graph showing progressive depletion of radiolabeled gp120 substrate in the presence of increasing concentrations of Lay2 L chain.

Immunoblotting of reducing gels with an anti-gp120 antibody that recognizes proteolytic breakdown products of the protein (Pollard, S., et al., Proc. Natl. Acad. Sci. USA 88:11320–11324 (1991)) yielded well-defined product bands generated by Lay2. See FIG. 2B. Increasing hydrolysis of gp120 was evident at increasing Lay2 concentrations, as shown in FIG. 3, estimated as the reduction in intensity of the 120 kD substrate band. This was accompanied by increasing accumulation of the 80 kD and other cleavage products.

Preliminary estimates of the kinetics of the reaction obtained by incubation of 20 nM Lay2 with increasing concentrations of Lay2 (10–300 nM) yielded initial rates that could be fitted to the Michaelis-Menten equation. The apparent Km value of the reaction was 30 nM and Vmax was 0.06 nmol gp120 /nmol Lay2/h. The comparatively high affinity of gp120 for Lay2 is shown by observations that trypsin-catalyzed hydrolysis analyzed in parallel reactions was nonsaturable at concentrations up to 1 $\mu$M, suggesting that the Km of trypsin for gp120 is substantially greater than that of Lay2.

Figure 2:
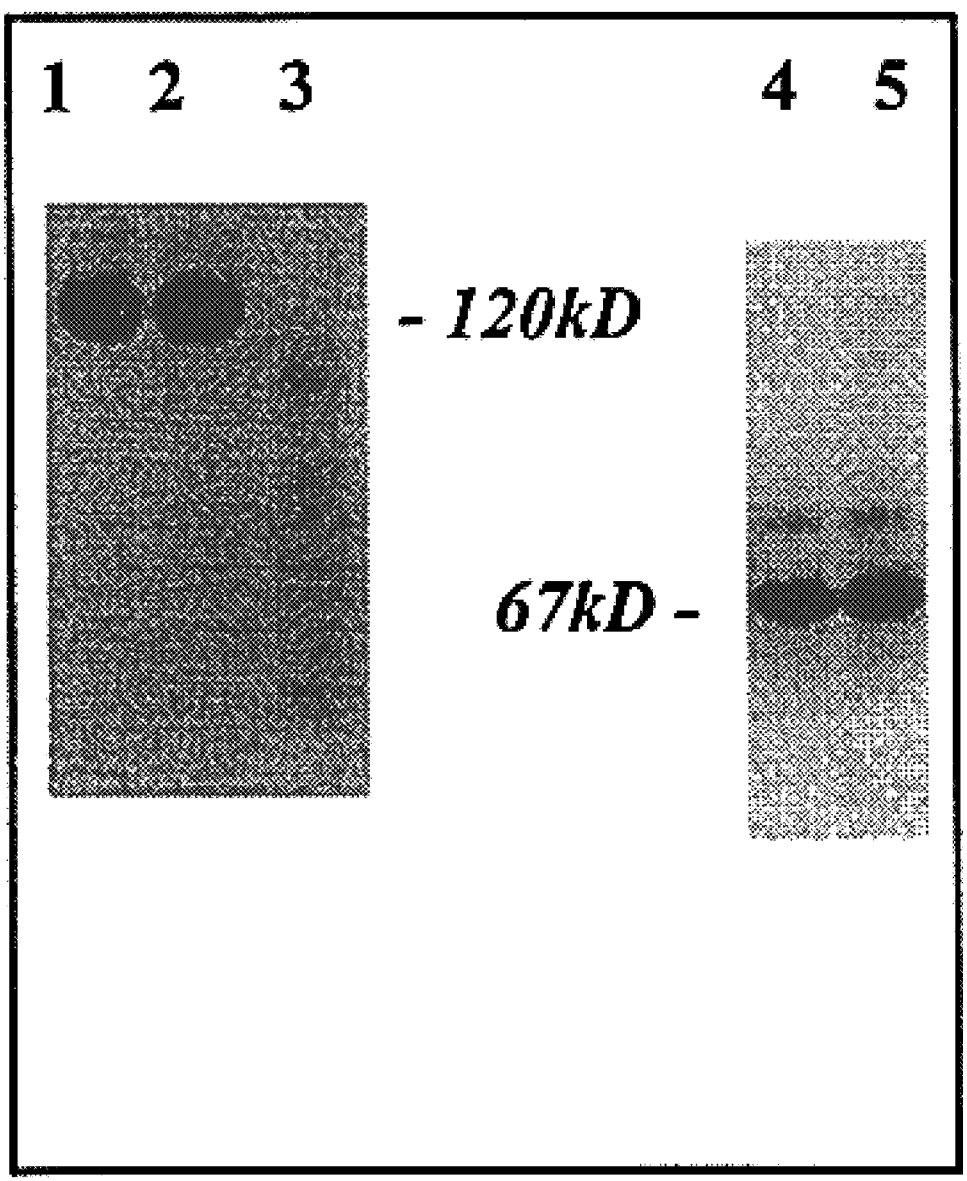
FIG. 2A is an autoradiogram illustrating hydrolysis of radiolabeled gp120 incubated with Lay2-L chain for 6 hours at 37° C.
FIG. 2B is a silver-stained SDS-page gel illustrating hydrolysis of unlabeled gp120 by Lay2 L chain.

There was no hydrolysis of $^{125}$I-albumin by Lay2, suggesting that the observed gp120 hydrolysis is not a nonspecific phenomenon, FIG. 2A. Increasing concentrations of VIP inhibited hydrolysis of $^{125}$I-gp120 by Lay2 (apparent Ki of VIP, 620 nM). Lay2 also hydrolyzed radiolabeled VIP, with a Km of 144 nM. Based on a comparison of its Km for gp120 and Ki/Km for VIP, Lay2 appears to bind gp120 about 5–21 fold more strongly than VIP. gp120 has two short regions of homology with VIP (LaRosa, G. J., et al., Science 149:932–935 (1990); Gorny, M., et al, J. Immunol. 150:635–643 (1993)), which might underlie reactivity of both polypeptides with Lay2.

Figure 4:
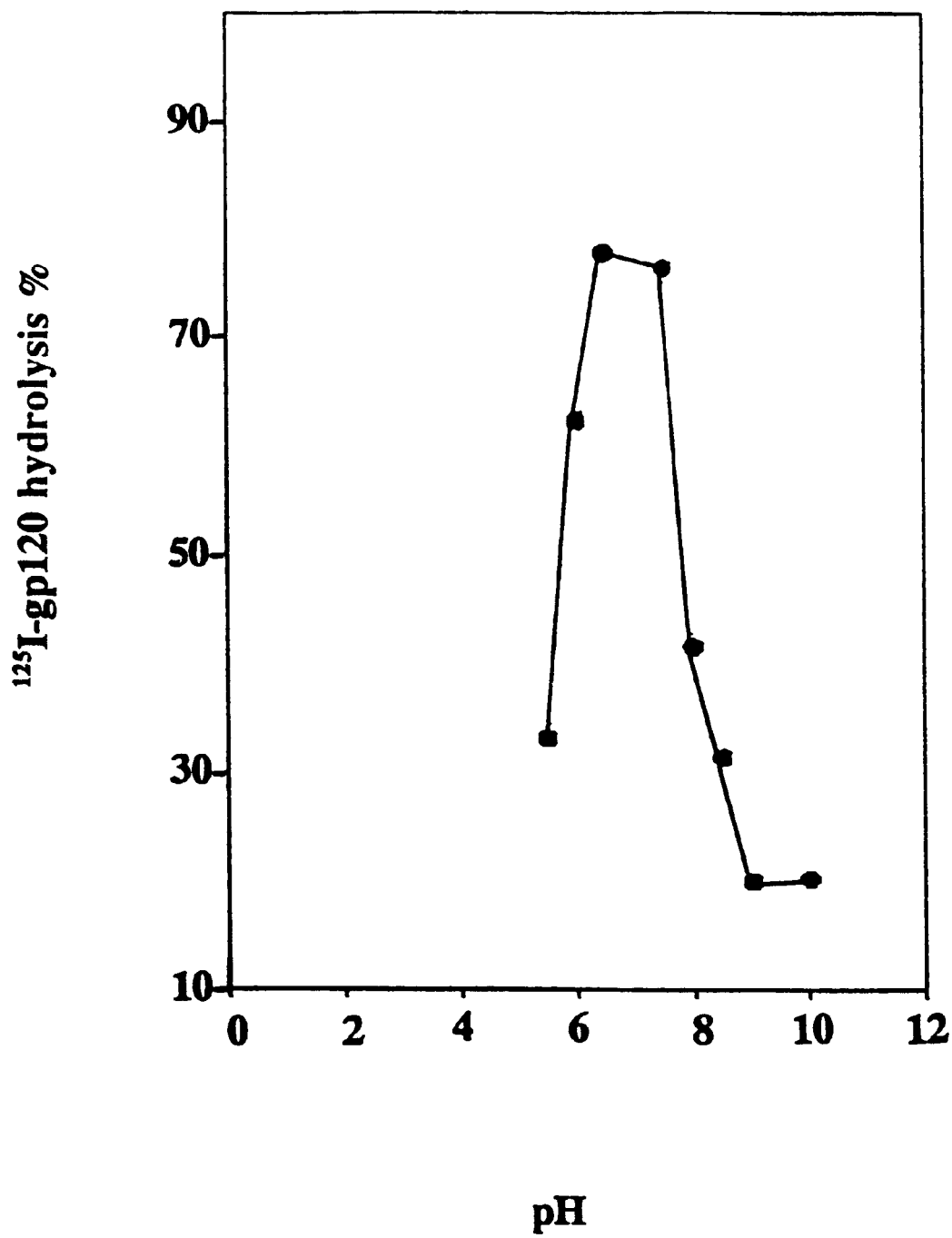
FIG. 4 is a graph depicting the pH dependence of Lay2 L chain catalyzed hydrolysis of radiolabeled gp120.

The optimal pH for the gp120 hydrolysis by Lay2 was in the neutral range, as illustrated in FIG. 4, suggesting the involvement of amino acid residues with neutral pKa values as the catalytic residues (Ser, Thr, Tyr, His). In the presence of a serine protease inhibitor (0.3 mM diisopropyl fluorophosphate), Lay2-catalyzed hydrolysis was essentially completely inhibited. In comparison, inhibitors of metalloproteases, cysteine proteases and acid proteases (EDTA, iodoacetamide, Pepstatin A) were without effect on the reaction. These observations suggest that a Ser residue may be involved in gp120 hydrolysis.

The sequence of Lay2 has been determined. Lay2 is a member of the kappa IIc subgroup. The number of Ser/Thr residues in the CDRs of this L-chain is unusually high. Site-directed mutagenesis of a catalytic anti-VIP L-chain has showed that its Ser27a and His93 are the catalytic residues. A Ser residue is also present at position 27a in Lay2. Position 93 in Lay2 is occupied by Glu (instead of His in the anti-VIP L-chain). In a preliminary model of Lay2 generated using the computer program AbM (Martin, A. C. R., et al., Proc. Natl. Acad. Sci. USA 86:9268–9272 (1989)), Ser27a and Glu93 are within hydrogen bonding distance (2.9 angstroms). If these residues are hydrogen bonded, the resultant increase in the nucleophilicity of the Ser residue may permit its participation in peptide bond hydrolysis by a mechanism analogous to that occurring in serine protease catalysis.

Figure 5:
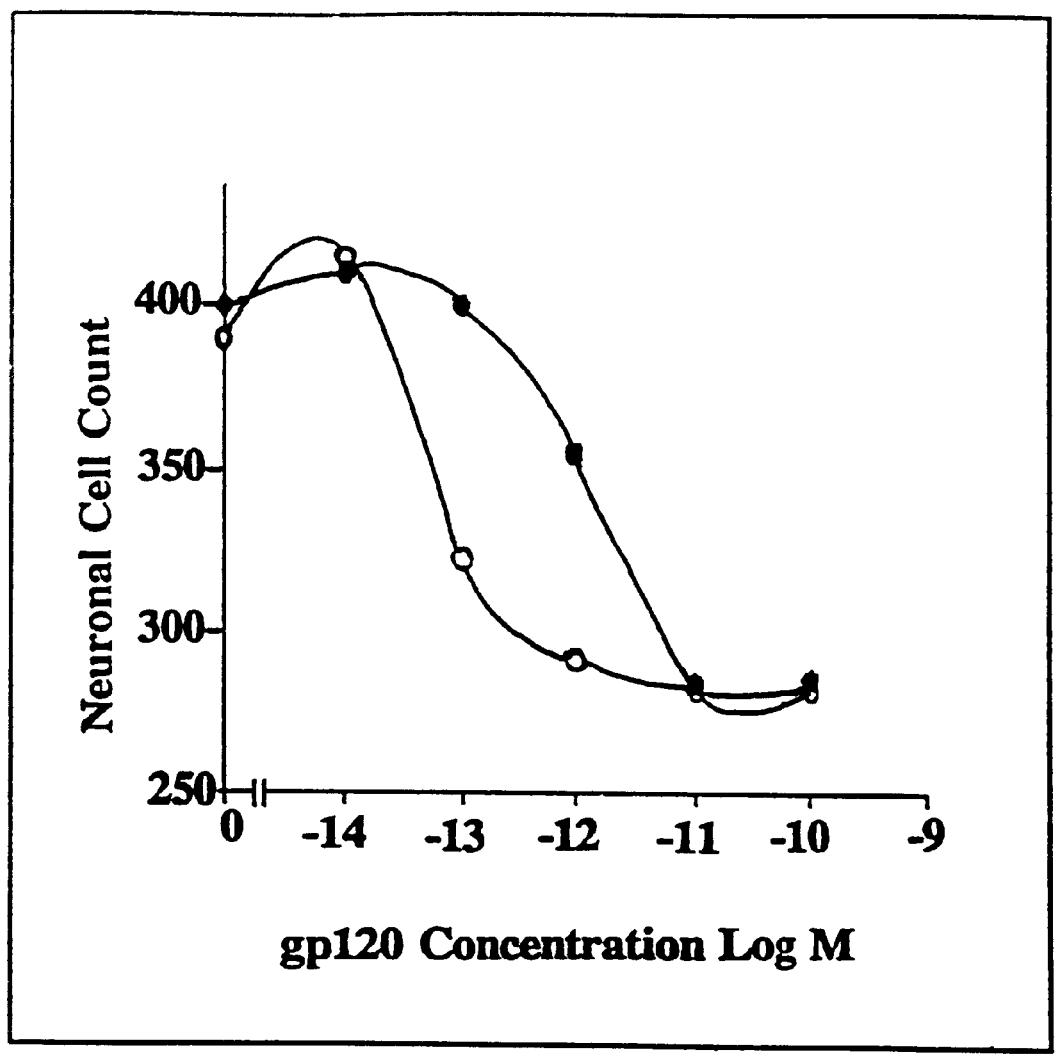
FIG. 5 is a graph showing the reduction of neurotoxicity of gp120 on neuronal cells following treatment with Lay2 L chain.

The effects of control gp120 and gp120 treated with Lay2 (10 μM, 30 hours) on the viability of cultured mouse cerebral cortical cells were compared. As reported previously (Brenneman, D. E., et al., Nature 335:639–642 (1988)), sub-picomolar concentrations of control gp120 were toxic for these cells. Briefly, cerebral cortical cells were prepared from newborn Wistar rats using 0.25% trypsin to dissociate the tissue. Cells were cultured in MEM medium supplemented with 10% fetal calf serum. After 2 days, about 80% of the cells are neurons and about 20% are glial fibrillary acidic protein positive astrocytes. Following treatment with Lay2, the potency of gp120 was reduced by more than 10-fold, corresponding directly to the level of hydrolysis. See FIG. 5. Electrophoresis and silver-staining of the Lay2-treated gp120 showed that about 85% of the protein had been digested. Control Lay2 without gp120 did not display a neurotoxic effect.

Figure 6:
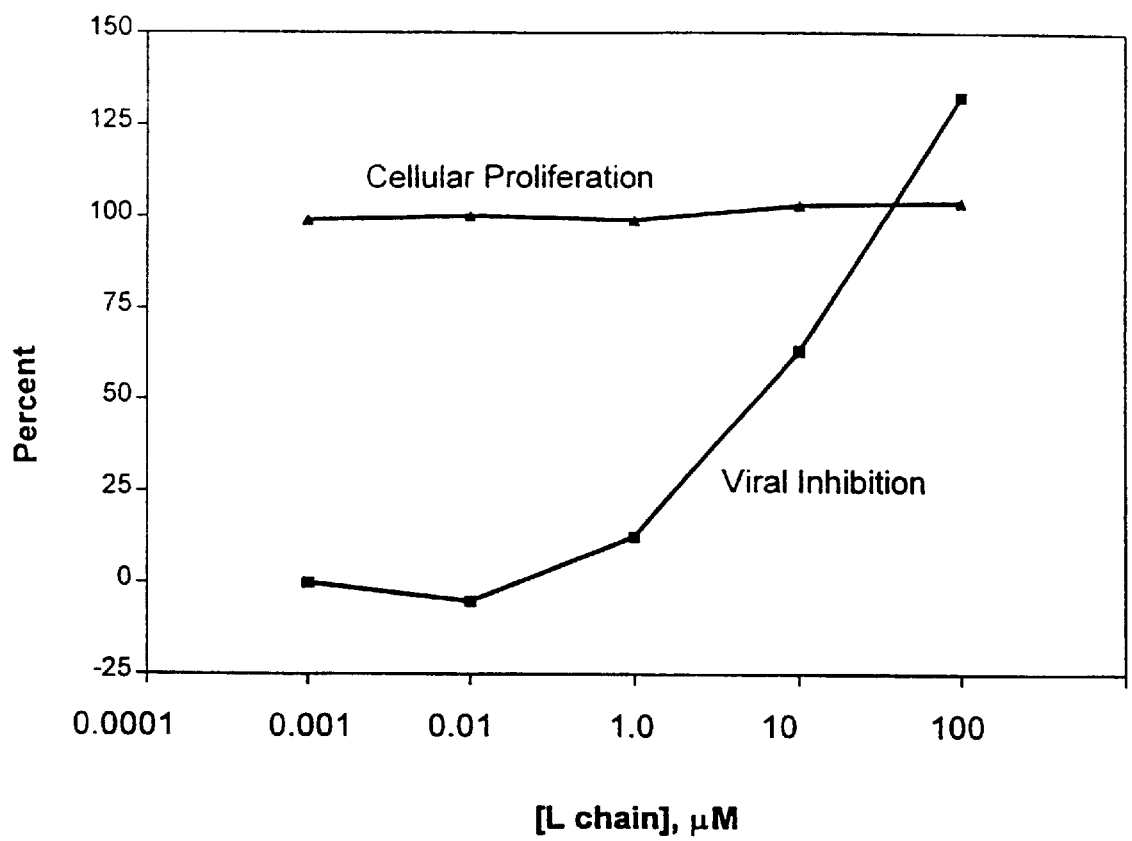
FIG. 6 is a graph illustrating inhibition of HIV-1 infectivity by pretreatment with Lay2 L chain.

Lay 2 was assayed for its ability to inhibit HIV-1 infectivity. Under serum-free conditions, pretreatment with this catalytic L chain indeed inhibited infection of MT-2 cells, a T-cell line, by HIV-1 (IIIB), as determined by microscopic observation for cytopathic effects (syncytium formation) and the microculture tetrazolium (MTA) assay using 2,3 bis(2-methoxy-4-nitro-5-sulfophenyl) 5-[(phenylamino)-2H-tetrazolium hydroxide. See FIG. 6. The multiplicity of infection (MOI) in this experiment was 3.2. At lower MOI values, the L chain is likely to display even better potency. Treatment of the cells with the L chain in the absence of HIV-1 did not produce a cytopathic effect. These results indicate that the L chain is capable of recognizing and cleaving native gp120.

EXAMPLE II

PREPARATION OF RECOMBINANT LAY2 $V_L$

As mentioned previously, the human Bence Jones protein designated Lay2 was provided by Dr. Alan Solomon, University of Tennessee and was collected from a patient who is now deceased. The need for a replenishable supply of the catalyst has been met by constructing a recombinant form of Lay2 in a bacterial expression system. This is expected to permit engineering of derivatives of Lay2 with improved catalytic characteristics.

Successful cloning and isolation of a catalytic L chain with activity against vasoactive intestinal peptide has been described in U.S. Pat. No. 5,229,272, the entire disclosure of which is incorporated by reference herein.

The sequence of the variable domain of the Lay2 L-chain has been previously determined in Dr. Solomon's laboratory. The V-exon encoded portion varies from that of one of the three germline genes (O11-01) (Klein, R., et al., Eur. J. Immunol. 23:3248–3271 (1993)) that encode the human II L-chain family at six positions. Of these differences, presumably reflecting somatic mutations, one involves a CDR position. At position 92 in CDR3, Lay2 has a Leu residue rather than Ile. The remaining five differences between the Lay2 protein and the germline gene O11-01 involve FR sites distant from the CDR segments; Lay2 also has an additional residue, Glu, at position 0, representing a seventh variance of unknown significance. The similarity between the Lay2 sequence and the O11-01 germ line sequence is noteworthy, in that it may reflect the capability of other $V_L$ domains derived from this germ line gene to bind and hydrolyze gp120.

Figure 7:
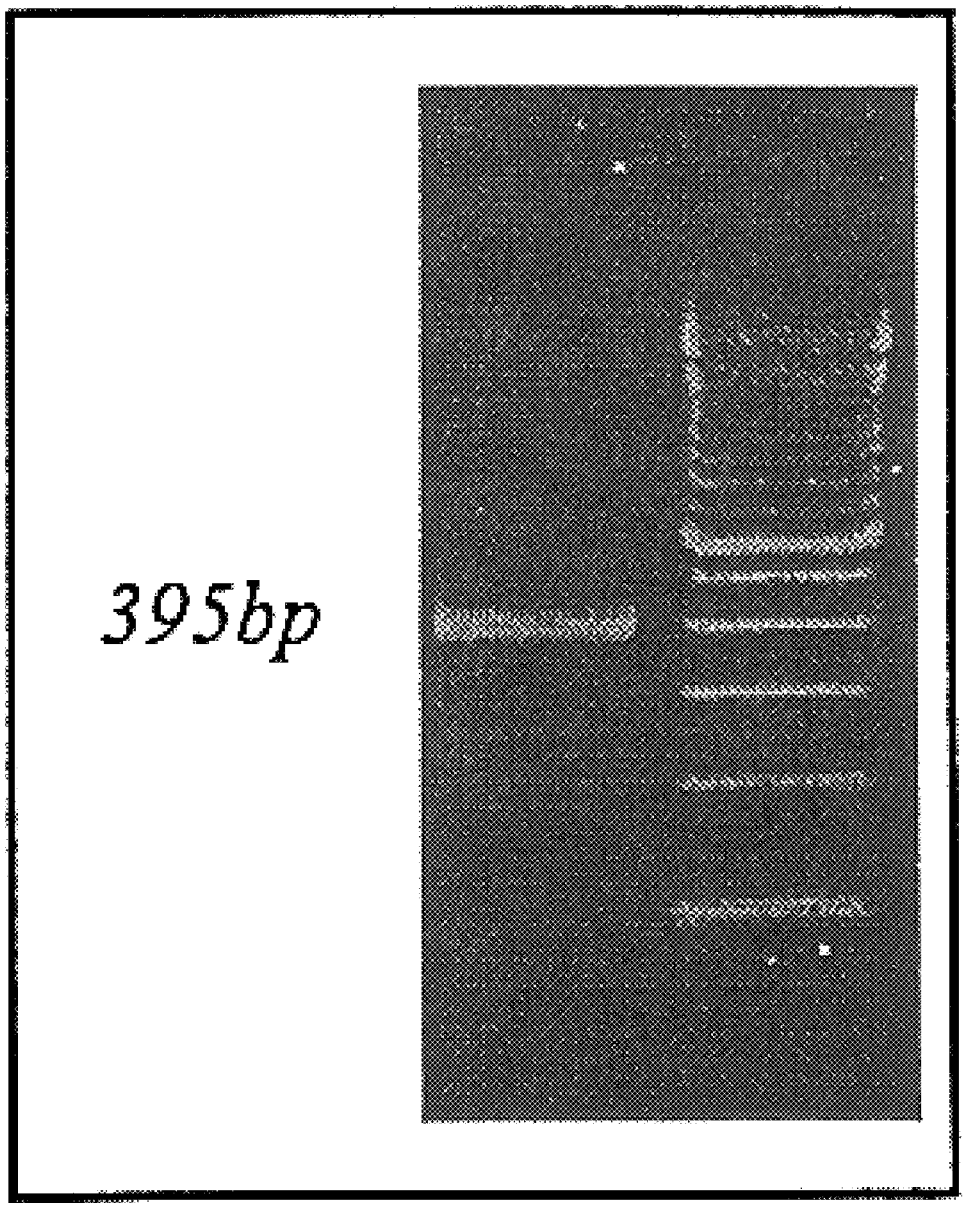
FIG. 7 is a gel showing the size of the cDNA encoding the Lay2 $V_L$ domain synthesized by recursive PCR.

The cDNA encoding the Lay2 $V_L$ domain protein has been synthesized by recursive PCR. See FIG. 7. The fully functional recombinant form of the protein may be expressed as described below. These methods have previously been used to successfully construct genes that encode human variable domains (Wilkins-Stevens, P., et al. Prot. Science 4:421–432 (1995)). Briefly, construction of the $V_L$ domain cDNA involves the use of recursive PCR (Prodromou, C., et al., Prot. Eng. 5:827–829 (1992)) to conjoin eight overlapping synthetic oligonucleotides that provide codons spanning the entire $V_L$ domain, an N-terminal signal sequence and flanking sequences that contain SfiI and NotI restriction sites to allow insertion into the expression vector. The cDNA also includes a short C-terminal linker segment for use in constructing an Fv.

EXAMPLE III

ISOLATION OF GP120 CATALYTIC ANTIBODIES FROM AIDS AND SLE PATIENTS AND RECOMBINANT PRODUCTION THEREOF

The L chain described in the preceding section was isolated by random screening of multiple myeloma patients. It is known that catalytic antibodies are formed at high levels in autoimmune diseases like lupus, and gp120 binding antibodies have been found in SLE patients. This observation has prompted us to analyze the sera of HIV-1 positive patients and lupus patients for the presence of catalytic antibodies to gp120.

The IgG fraction purified from the serum (~0.5 ml) of AIDS patients and SLE patients was purified by DEAE-cellulose chromatography (DE52 matrix, Whatman) or Protein G-Sepharose (Pharmacia) in 50 mM Tris-HCl, pH 7.5, 0.002% sodium azide. The IgG fractions were obtained as the unbound material from the DEAE-cellulose column and as the acid eluted protein from the Protein G column. Elution was performed using 100 mM glycine, pH 2.7, followed by neutralization of the solution with 1M Tris base, pH 9.0. Since IgG preparations are known to contain small amounts of free L chains, the DEAE-cellulose purified IgG was subjected to further chromatography on a high performance gel filtration column (Superose-12, Pharmacia) in 50 mM Tris-HCl, 100 mM glycine, 150 mM NaCl, 0.025% Tween-20, 0.02% sodium azide, pH 7.5 (flow rate 0.5 ml/minute; fraction size 0.5 ml). L chains present in the DEAE-cellulose purified IgG were identified as the fraction eluting at mass 25 kD based on column calibration with standard proteins with known mass. Protein concentrations were obtained by measurement of ultraviolet light absorbance at 280 mn (0.8 mg/ml protein solution gives a reading of 1.0 optical density at 280 nm using a 1 cm path length cuvette). gp120 cleavage was measured by SDS-electrophoresis and autoradiography as described in the preceding section.

The sera described above are polyclonal. Resolution of individual L chains may be performed using two dimensional gel electrophoresis followed by electroelution of single L chains. Once monomer L chains are isolated, amino terminal peptide sequencing would be performed to generate specific oligonucleotide probes for cloning purposes.

Figure 8:
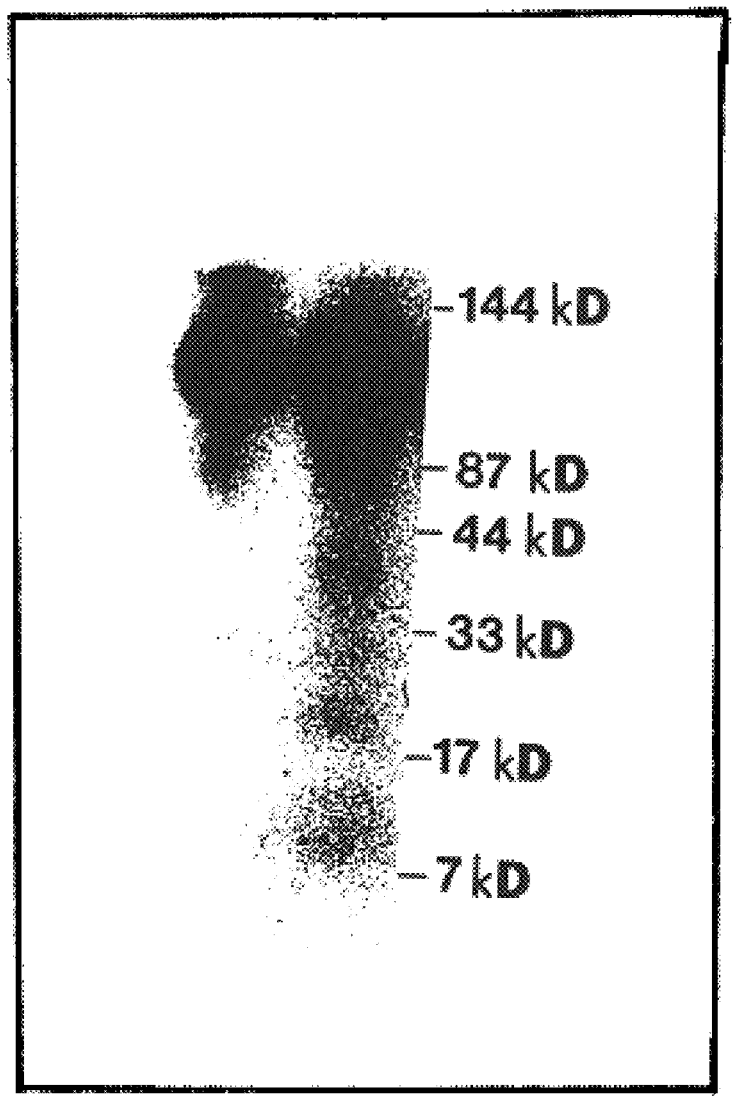
FIG. 8 is an autoradiogram showing hydrolysis of radiolabeled gp120 by L isolated from an SLE patient.

FIG. 8 shows that incubation of $^{125}$I-gp120 (2 nM) with protein G sepharose purified IgG (3 μM) from an SLE patient (laboratory code #530) for 18 hours at 37° C. resulted in appearance of cleavage products of gp120 corresponding to a smear at about 110 kD and resolved bands at mass 37 kD, 24 kD and 10 kD. The intact gp 120 is evident as the 120 kD band. The 110 kD smear may be a mixture of polypeptides or it may be a single product that is too close in mass to intact gp120 to permit its clean separation by the experimental procedures applied in this experiment.

Figure 9:
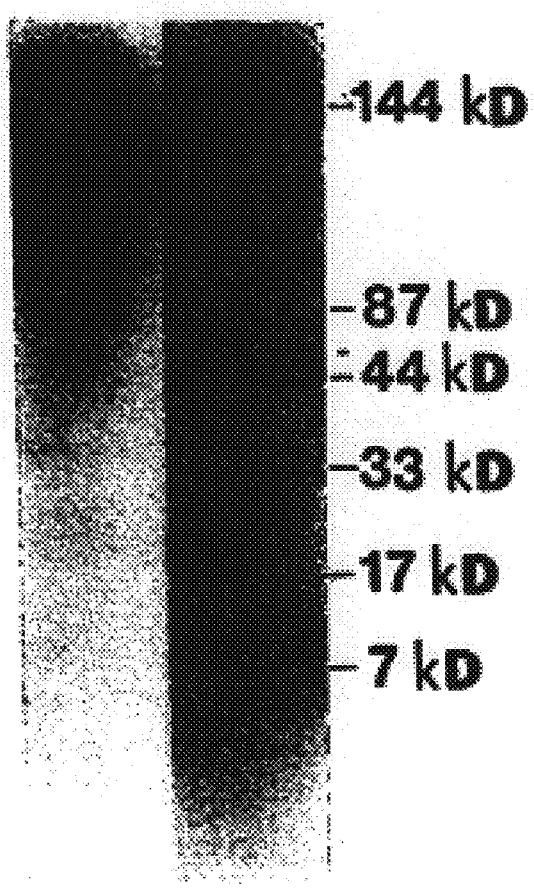
FIG. 9 is an autoradiogram showing hydrolysis of radiolabeled gp120 by L chains isolated from an HIV patient.

FIG. 9 shows the incubation of $^{125}$I-gp120 (2 nM) with L chains purified from an HIV positive patient (laboratory code number #005) for 17 hours at 37° C. resulted in the appearance of cleavage products of gp120 corresponding to 90 kD, 25 kD, 12 kD and <10 kD. Similar L chain fractions from HIV negative controls did not display the gp120 cleaving activity. It is known that the concentrations of L chains in IgG preparations like the one used for the gel filtration in this experiment are very small. SDS-electrophoresis and silver staining showed that the L chain concentration in this IgG fraction was <1.5%. The specific activity (% cleavage of gp120/protein concentration) of the L chains used as catalysts can be calculated, therefore to be at least 112-fold greater than that of the Lay2 catalytic antibody L chain described in the preceding section.

These observations demonstrate that the synthesis of L chains with gp120 cleaving activity may be a fairly common component of the immune response in HIV-1 and SLE afflicted patients. A replenishable supply of the L chains can be obtained by cloning the immune repertoire of the above referenced patients employing techniques that have been successful in the isolation of VIP cleaving L chains from an asthma patient as described in Gao et al., In *Antibody Engineering Protocols*, pages 51:286–291, ed. S. Paul, Humana Press, Totowa, N.J., (1995).

Rare antibodies can be rapidly isolated by ligand-specific affinity chromatography of phage particles displaying recombinant antibody fragments on their surface as geneIII fusion proteins. A V L-chain phage display library has been prepared from the peripheral blood lymphocytes of an asthma patient (Tyutyulkova, S., et al., Appl. Biochem. Biotech. 47:191–198 (1994); Tyutyulkova, S., et al., In *Antibody Engineering Protocols*, pages 5121:377–394, ed. S. Paul, Humana Press, Totowa, N.J., (1995). In these experiments, phage particles with VIP binding activity were enriched by affinity chromatography on immobilized VIP. Two VIP binding L chains were expressed in soluble form in *E. coli*, their primary structure deduced by cDNA sequencing and the proteins purified to electrophoretic homogeneity by metal chelating and protein L affinity chromatography.

The proteolytic activity of the L chains was measured using (Tyr10-$^{125}$I)VIP substrate. With increasing concentrations of the recombinant L chains, a linear increase in VIP hydrolysis was evident. The reaction for both L chains displayed saturation kinetics with respect to the substrate concentration. The kinetic efficiencies (kcat/Km) using VIP as substrate were better or comparable to that of trypsin, a highly evolved protease. The L chains did not catalyze the cleavage of resorufin, a nonspecific protease substrate. The monomer form of the L-chain was responsible for hydrolysis of VIP, shown by elution of the activity at ~26 kD from a gel filtration column.

Similar methods may be adapted to clone and express the L chains of the HIV and SLE patients described above. Peripheral blood lymphocytes would be collected, and L chain cDNA prepared by the reverse transcriptase-PCR method. The PCR products would then be cloned into the phagemid vector pCANTABhis6, which allows display of L chains on the surface of phage particles or their expression as soluble proteins. Following electroporation of competent *E. coli* TG1 cells with the phagemid DNA, phage particles displaying L chains fused to protein 3 were rescued by superinfection with VCSM13 helper phage, precipitated with polyethylene glycol and subjected to affinity chromatography on a gp120-sepharose column. Clones will be isolated by low pH elution and tested for gp120 binding by radioimmunoassay and/or ELISA. The clones would be grown in *E. coli* cells and the cultures induced with IPTG (1 mM) for 24 hours to permit secretion of soluble L chains into the supernatant. L chains may also be expressed in the periplasmic space by reducing the induction period with IPTG from 24 to 3 hours.

As mentioned previously, catalytic antibodies are synthesized in response to immunization with substrate. An antibody L-chain library has been cloned from a mouse immunized with VIP. The proteolytic activity of L-chain clones selected randomly or selected based on their antigen-binding activity was determined. Selection was done by chromatography of phages on immobilized VIP. Potent catalysts capable of hydrolyzing (Tyr10-$^{125}$I)VIP and generic protease substrates (peptide-methylcoumarinamides) were isolated. The clones selected based on their VIP-binding activity displayed improved catalysis by 1–2 orders of magnitude. The increase in catalytic activity was due to increased VIP-binding affinity. Turnover numbers using VIP as substrate ranged from 0.1–2.2/min. Approximately 20% of purified L chains from 156 randomly selected clones assayed at 10 nM protein displayed catalytic activity using a synthetic peptide as substrate. The variable region of twelve L-chain clones has been sequenced and consensus sequences and spatial motifs associated with catalytic activity are now sought. These observations show frequent catalysis by the natural antibody L-chain repertoire and the development of antigen-specific catalytic activity by immunization with a polypeptide. This may occur by de novo development of catalytic activity due to variable region sequence diversification or its inheritance as a germ line activity and maintenance during maturation of high affinity for the immunogen.

Infection with HIV-1 induces a massive immune response. Cloning of an L chain library from the lymphocytes of the patient described above using the methodology set forth herein for VIP L chain cloning would also prove successful in isolating a replenishable supply of anti-gp120 hydrolyzing antibody L chains.

EXAMPLE IV

TREATMENT OF PATIENTS WITH THE GP120 HYDROLYZING L CHAINS OF THE INVENTION

The catalytic anti-gp120 L chain antibodies may be administered to patients in a suitable pharmaceutical excipient to reduce levels of soluble gp120 antigen in the body.

The clinical use of immunoglobulin for intravenous administration (IVIG) has been reviewed in detail. See for example Dietrich et al., Blood 79:2946–51 (1992); Rossi et al., Immunol. Rev. 110:135–149 (1989); Dwyer, J. M., New Eng. J. Med. 326:107–16, (1992); Schwartz, S. A., J. Clin. Immunol. 10:81 (1990).

The purified gp120 hydrolyzing L chains of the instant invention would be administered by i.v. to patients to reduce the levels of HIV-1 and soluble gp120 in the body. Dosages would be adjusted according to the viral burden in the patient and may range between 1/100th of the viral burden to stoichiometric (1:1) levels. Because the L chains are catalytic, substantially lower dosages may be required for viral neutralization. It is known that dosages of IgG ranging from 0.25–1 g/kg of body weight are safe. Efficacy would be measured by analyzing the levels of soluble gp120 before and after treatment by ELISA.

Alternatively, the anti-gp120 hydrolyzing antibodies of the invention would be directly administered to the brains of patients afflicted with AIDS related dementia. The delivery of therapeutic agents to the brain has been described in the literature. See for example Harbaugh, R. E., Biomed. Pharmacother. 43:483–485 (1989); Johnson et al., J. Neurosurg. 70:240–248, 1989); Giannone, L., et al., J. Clin. Oncol. 4: 68–73 (1986).

The gp120 hydrolyzing light chains may be delivered directly to the intraventricular compartment via a cannula or alternatively they may be conjugated to a transferrin molecule and delivered via i.v. The construction of fusion proteins is well known in the art. The genetic sequences encoding the catalytic L chain of the invention would be operably linked to the genetic sequences encoding transferrin. Transferrin has been shown to be capable of crossing the blood brain barrier and thus may effectively deliver the L chain of the invention to the brain (Shin et al., Proc. Natl Acad. Sci. 92:2820–2824 (1995).

While certain of the preferred embodiments of the present invention have been described and specifically exemplified above, it is not intended that the invention be limited to such embodiments. Various modifications may be made thereto without departing from the scope and spirit of the invention, as set forth in the following claims.

What is claimed is:

1. An isolated, naturally occurring, catalytic antibody or catalytic component thereof which catalyzes the cleavage of a peptide bond in gp120 of human immunodeficiency virus type 1 (HIV-1).

2. The isolated, naturally occurring, catalytic component of claim 1, wherein the component is selected from the group consisting of Fab fragments, Fv fragments, light chains and light chain dimers.

3. The antibody component of claim 2, wherein the component is a light chain.

4. The antibody component of claim 2, wherein the component is an Fv comprising a light chain which cleaves gp120.

5. The catalytic antibody or catalytic component thereof of claim 1, wherein said antibody or component is isolated from serum.

6. The catalytic antibody or catalytic component thereof of claim 5, wherein said serum is obtained from a patient infected with HIV-1.

7. The catalytic antibody or catalytic component thereof of claim 5, wherein said serum is obtained from a patient with systemic lupus erythematosus (SLE).

8. A composition comprising the isolated, naturally occurring, catalytic antibody or catalytic component thereof of claim 1.

9. A method for isolating a catalytic antibody which catalyzes the cleavage of gp120 of HIV-1, said method comprising the steps of:

a) screening serum samples for the presence of said catalytic antibody as assayed by the generation of cleavage products of said gp120 lower than 120 kD; and b) purifying said catalytic antibodies.

10. A method for isolating a catalytic antibody component which catalyzes the cleavage of gp120 of HIV-1, said component selected from the group consisting of light chains and light chain dimers, said method comprising the steps of:

a) screening serum samples for the presence of said catalytic antibody component as assayed by the generation of cleavage products of said gp120 lower than 120 kD; and b) purifying said catalytic antibodies.

11. A method for isolating a catalytic antibody light chain which catalyzes the cleavage of gp120 of HIV-1, said method comprising the steps of:

a) screening serum samples for the presence of said catalytic antibody light chain as assayed by the generation of cleavage products of said gp120 lower than 120 kD; and b) purifying said catalytic antibody light chain.

12. The method of claim 9, 10 or 11 wherein said serum is obtained from a patient infected with HIV-1.

13. The method of claim 9, 10 or 11 where in said serum is obtained from a patient with SLE.

14. A method for preparing a catalytic antibody component which cleaves gp120 of HIV-1, said component being selected from the group consisting of an Fv fragment, a light chain, and a light chain dimer, said method comprising the steps of:

a) determining the genetic sequence of the catalytic antibody component;

b) inserting into a cell a nucleic acid having the sequence as determined in step a encoding said catalytic antibody component;

c) expressing said catalytic antibody component in said cell; and d) recovering said catalytic antibody component from said cell.

15. A method for the production of a catalytic antibody light chain which catalyzes the cleavage of gp120 of HIV-1, said method comprising the steps of:

a) obtaining an isolated catalytic antibody light chain according to the method of claim 11;

b) determining the genetic sequence of said isolated catalytic antibody light chain;

c) synthesizing an overlapping series of oligonucleotides representing sections of the genetic sequence of said catalytic antibody light chain;

d) operably linking said overlapping series of oligonucleotides such that a nucleic acid comprising the genetic sequence of a complete catalytic antibody light chain is obtained;

e) transforming a cell with said nucleic acid;

f) expressing said catalytic antibody light chain in the cell;

g) recovering said catalytic antibody light chain from the cell.

16. The method of claim 14 or 15, wherein said cell is selected from the group consisting of a bacteria, a fungus, a yeast, a mold, an animal cell, a protozoan cell and a plant cell.

17. The method of claim 14 or 15, wherein said nucleic acid is subjected to mutagenesis before insertion into said cell.

* * * * *

UNITED STATES PATENT AND TRADEMARK OFFICE
CERTIFICATE OF CORRECTION

PATENT NO.   : 6,156,541
DATED        : December 5, 2000
INVENTOR(S)  : Sudhir Paul et al.

It is certified that error appears in the above-identified patent and that said Letters Patent is hereby corrected as shown below:

Column 1,
Line 8, please insert the following paragraph:

-- Pursuant to 35 U.S.C. §202(c) it is acknowledge that the U.S. Government has certain rights in the invention described herein, which was made in part with funds from the National Institute of Health, Grant Numbers AI31268 and TW00287. --

Signed and Sealed this

Eleventh Day of March, 2003

JAMES E. ROGAN
*Director of the United States Patent and Trademark Office*